US007373204B2

(12) United States Patent
Gelfand et al.

(10) Patent No.: US 7,373,204 B2
(45) Date of Patent: May 13, 2008

(54) IMPLANTABLE DEVICE AND METHOD FOR TREATMENT OF HYPERTENSION

(75) Inventors: Mark Gelfand, New York, NY (US); Howard R. Levin, Teaneck, NJ (US)

(73) Assignee: Lifestim, Inc., Mt. Olive, NJ (US)

( * ) Notice: Subject to any disclaimer, the term of this patent is extended or adjusted under 35 U.S.C. 154(b) by 154 days.

(21) Appl. No.: 10/921,162

(22) Filed: Aug. 19, 2004

(65) Prior Publication Data
US 2006/0041283 A1 Feb. 23, 2006

(51) Int. Cl.
*A61N 1/18* (2006.01)
*A61N 1/32* (2006.01)

(52) U.S. Cl. .............................. 607/44; 607/2; 607/48; 128/907

(58) Field of Classification Search .................. 607/44, 607/2, 48; 128/907
See application file for complete search history.

(56) References Cited

U.S. PATENT DOCUMENTS 5,707,400 A * 1/1998 Terry et al. .................... 607/44
5,876,360 A * 3/1999 Liu ............................ 601/154
2001/0001125 A1* 5/2001 Schulman et al. ............. 607/2
2002/0133210 A1* 9/2002 Gruzdowich et al. ......... 607/44
2003/0004549 A1* 1/2003 Hill et al. ...................... 607/9
2004/0102818 A1* 5/2004 Hakky et al. ................. 607/44

FOREIGN PATENT DOCUMENTS

GB 2156679 A * 10/1985

OTHER PUBLICATIONS

Yanling F. The Treatment of Hypertension by Acupuncture. First Internation Symposium Hypertension 1996: One Medicine, Two Cultures Compared Medicines.*

* cited by examiner

*Primary Examiner*—Carl Layno
*Assistant Examiner*—Tammie K. Heller
(74) *Attorney, Agent, or Firm*—Fitch, Even, Tabin & Flannery

(57) ABSTRACT

A method and apparatus for treatment of hypertension with electrostimulation of peripheral nerves. Treatment is performed by periodically stimulating a nerve such as a median nerve. Apparatus for stimulation is permanently implanted in the body. The nerve is stimulated by electric current applied to electrodes that are placed near the target nerve or the muscle innervated by the target nerve.

15 Claims, 11 Drawing Sheets

IMPLANTABLE DEVICE AND METHOD FOR TREATMENT OF HYPERTENSION

FIELD OF THE INVENTION

This invention relates to methods and apparatus for controlling hypertension by stimulating one or more peripheral nerves. It also relates to the field of invasive nerve stimulation using an implantable nerve stimulator with implantable electrodes. It also relates to controlling nerve stimulation based on physiologic feedbacks.

BACKGROUND OF THE INVENTION

Hypertension

It is generally accepted that high blood pressure (HBP, also called hypertension) is bad, but most people don't know why, and what the term really means. In fact, all humans have high blood pressure some of the time, and we wouldn't be able to function if we didn't (such as during exercise). High blood pressure is only of concern when it persists for long periods of time or is extremely high over a very short (hours) period of time. Its adverse effects usually take many years to develop. Clinically important HBP is very common. According to official government figures it affects 50 million people in the United States.

While everyone has high blood pressure some of the time, many people live their entire lives with moderately high blood pressure and never know it until it is notice on a routine visit to the doctor. Unfortunately, not all people are so lucky. In these people, high blood pressure significantly increases the risk of a number of serious events, mainly strokes and heart attacks.

More specifically, the damage caused by high blood pressure is of three general sorts. The first is the one everyone thinks of—bursting a blood vessel. While this is dramatic and disastrous when it happens, it's actually the least common of the three problems. It occurs most frequently in the blood vessels of the brain, where the smaller arteries may develop a weak spot, called an aneurysm. This is an area where the wall is thinner than normal and a bulge develops. When there is a sudden surge of pressure the aneurysm may burst, resulting in bleeding into the tissues. If this occurs in the brain, it is called a stroke. In contrast, if this happens to the aorta (the main blood vessel in the body), it is called a ruptured aortic aneurysm. Both of these events can lead to permanent damage and death.

The second adverse consequence of high blood pressure is that it accelerates the deposition of cholesterol in the arteries forming a blockage (atheroma). This problem, too, takes many years to develop, and it is very difficult to detect until it causes a major blockage. The most important sites to be affected are the heart, where the blockage can cause angina and heart attacks; the brain, where it causes strokes; the kidneys, where it causes renal failure (and can also make the blood pressure go even higher); and the legs, where it causes a condition known as intermittent claudication, which means pain during walking and may even lead to losing a limb.

Third, high blood pressure puts a strain on the heart: Because it has to work harder than normal to pump blood against a higher pressure, the heart muscle enlarges, just as any other muscle does when it is used excessively. Over a long period of time, the high blood pressure can lead to congestive heart failure, the most frequent cause for hospitalization in the United States.

Whatever the underlying cause, when the blood pressure reaches a certain level for a sufficient length of time it sets off a vicious cycle of damage to the heart, brain, and kidneys, resulting in further elevation of the pressure.

Classification of hypertension by its severity is somewhat arbitrary because there's no precise level of pressure above which it suddenly becomes dangerous. Historically, blood pressure has been primarily classified according to the height of the diastolic pressure. Someone whose diastolic pressure runs between 90 and 95 mm Hg may be regarded as having borderline hypertension, and when it's between 95 and 110 mm Hg it's moderate, and at any higher levels it's severe. Recent data suggests that the systolic pressure is as, and maybe more important than, diastolic blood pressure in determining the patient's risk for serious adverse events. Systolic hypertension is mainly seen in people over the age of 65 and is characterized by a high systolic, but normal diastolic, pressure (a reading of 170/80 mm Hg would be typical). It's caused by an age-related loss of elasticity of the major arteries. Another form of HBP, Labile hypertension, is a commonly used term for describing people whose pressure is unusually labile or variable. The most dangerous type of HBP is called malignant hypertension, or high blood pressure with evidence on physical exam that this pressure is causing an acute deleterious affecting on vital organ function. Malignant hypertension is regarded as an emergency requiring immediate treatment in a hospital. Not surprisingly, if untreated, malignant hypertension can be rapidly fatal. Because more people are treated nowadays than before, malignant hypertension is not common.

The objective of treatment is not simply to lower the blood pressure, but to prevent its consequences, such as strokes and heart attacks. According to the American Heart Association high blood pressure is present in 50,000,000 Americans (Defined as systolic pressure 140 mm Hg or greater, and/or diastolic pressure 90 mm Hg or greater, or taking antihypertensive medication). Of those with HBP, 31.6 percent are unaware they have it; 27.4 percent are on medication and have it controlled; 26.2 percent are on medication but don't have their HBP under control; and 14.8 percent aren't on medication. In most cases, high blood pressure can be controlled with one or a combination of oral drugs. Of those patients that take medication to control HBP, many suffer from debilitating side effects of these drugs such as heart arrhythmias, inability to exercise or do normal activities of daily living and impotence.

High blood pressure is usually treated with drugs. Several proposals have been made to treat blood pressure with electrical stimulus applied to various parts of the body.

Group 1: Controlling Hypertension With Highly Invasive Implantable Nerve Stimulation Several proposals have been made to treat moderately elevated blood pressure using highly invasive methods such as a vagal (part of the vagus nerve) nerve stimulation, spinal cord stimulation and deep brain stimulation. It has been known in the past that one can stimulate the vagal nerves by invasively dissecting the major nerve bundle and placing a spiral or enveloping nerve-type cuff around the nerve bundle. The nerve fibers are then directly stimulated by electrical field to achieve reduction in epilepsy, heart rate slowing, and potential blood pressure changes.

Currently, only nerve cuff-type electrodes or impalement-type electrodes are used for nerve stimulation, other than in the spinal cord. These types of electrodes can potentially cause irreversible nerve damage due to swelling or direct mechanical damage of the nerve. The placement of these electrodes either around the nerve bundle or into the neural perineum also poses a significant risk. The electrode placement is usually performed through very invasive surgery which in and of itself produces a high risk to nerve damage.

Terry, Treating Refractory Hypertension By Nerve Stimulation, U.S. Pat. No. 5,707,400 proposes implantation of an electrical coil or cuff around the vagus nerve, which runs superficially through the neck, and stimulation of the vagus nerve to lower high blood pressure.

Kieval, Devices and methods for cardiovascular reflex control, U.S. Pat. No. 6,522,926 and several other patents to the same author describe devices, systems and methods by which the blood pressure is reduced by activating baroreceptors. The baroreceptors are the biological sensors in the wall of the carotid artery that indicate to the brain an abrupt rise or fall of blood pressure by responding to the stretch of the arterial wall. In response to baroreceptor stimulation, the brain reduces the pumping of the heart with the consequential moderation of blood pressure. This phenomenon is known as the body's "baroreflex".

Obel, Implantable electrical nerve stimulator/pacemaker with ischemia for decreasing cardiac workload, U.S. Pat. No. 5,199,428 describes a method and apparatus for stimulating the right and/or left carotid sinus nerves or the right stellate ganglion or the epidural space of the spine electrical pulses in response to detected myocardial ischemia to decrease cardiac workload as a method to protect the myocardium.

The methods described above are potent and are capable of, at least temporarily, reducing blood pressure in a patient. They do not meet the objectives of the invention because they are highly invasive and have potentially debilitating or life threatening side effects. In general, it may be said that these methods attempt to regulate blood pressure by directly disturbing the vital parts of the central nervous system such as brain, spinal cord, vagus nerve and carotid sinus nerves. The potential side effects of such a device, including nerve damage, paralysis and death make the use of these methods unlikely except in the most severe cases where the high risk can be justified.

Group 2: Non-Invasive Nerve Stimulation to Treat Hypertension

All the devices that stimulate nerves non-invasively stem from traditional Chinese medicine use of acupuncture to treat essential hypertension (or HBP without an identifiable cause). Acupuncture has also been investigated for use in patients with essential hypertension in the Western countries. In spontaneously hypertensive rats, acupuncture-like electrical stimulation of thinly myelinated (Group III) somatic afferents activates central endorphin (natural opiate) pathways that elicit long-lasting decreases in sympathetic nerve activity (SNA) and blood pressure. Based on this data, the following major hypotheses can be argued: electroacupuncture (acupuncture with electric current) produces a long-lasting reduction in SNA, thereby providing a safe and effective complementary treatment of human hypertension. Pomeranz, et al, Electrotherapy Acupuncture Apparatus and Method, U.S. Pat. No. 4,566,064 describes an electroacupuncture device and mentions blood pressure as an indication for electroacupuncture.

Nevertheless, even if effective, acupuncture has little practical use. It requires frequent visits to the doctor for prolonged sessions that require commitment of time often impossible for working patients. Puncture of skin and manipulation of needles can be painful. It is also expensive. Several inventors proposed devices, based on acupuncture, that the patient could wear and use at home.

Zhu, Blood Pressure Depressor, U.S. Pat. No. 5,891,181 proposes electrical stimulation of nerves in the ear lobe to lower blood pressure.

Gruzdowich, Method of blood pressure moderation U.S. Pat. No. 6,393,324 describes a HBP control device in the form of a watch-like housing attachable to the human wrist by an adjustable attachment band. The device uses non-invasive nerve stimulation whereby electricity is passed through two electrodes to stimulate nerves located on the palm side of the wrist. The treatment provided by the device is based on the acupuncture of the P6 point, pericardium 6 point, or the master point of the pericardium meridian (sometimes referred to as the vascular meridian).

Non-invasive devices based on these inventions are available on the market and can be purchased without a prescription for reasonable price. These non-invasive devices are generally safe, require no surgery but are not very effective. Position of the electrodes over the particular point of a muscle or specific nerve is approximate and is easily disrupted. Skin has high resistance and high stimulation voltage is needed to achieve the therapeutic effect. Often pain from the electric stimulation is felt before blood pressure is reduced. Patients are required to take care of the device, turn it on and off, replace batteries and ensure that it is always placed correctly.

Group 3: Transvenous Nerve Stimulation to Control Heart Rate

Hill, U.S. Pat. No. 6,006,134, describes a method and device for electronically controlling the beating of a heart during cardiac surgery. Slowing the heart rate can result in a reduction of blood pressure. Hill proposed using venous electrical stimulation of nerve fibers, describes an electrostimulation device that includes a pair of electrodes for connection to at least one location in the body that affects or regulates the heartbeat. The invention is embodied in an external or implantable device which employs electrodes located on transvenous leads located in veins adjacent nerve fibers to be stimulated. The transvenous placement of stimulation leads reduces the invasiveness of the procedure.

Hill does not teach treatment of hypertension with an implantable device. Hill also does not point towards transvenous stimulation of peripheral nerves in an arm or a leg. Instead Hill proposes to simulate nerves of the heart and the vagus nerve, and admits that the stimulation may not only slow down but also stop the heart. Hill describes the electrodes that are placed on the catheter in an internal jugular vein several centimeters from the vagal nerve bundle. The amount of applied current for this type of stimulation will be too high to use in conscious patients since it may cause pain and muscle twitching. It is not therefore surprising that Hill proposed the transvenous stimulation during surgery, where patient is unconscious and constantly under observation.

SUMMARY OF THE INVENTION

In one embodiment, the invention provides an alternative method of controlling HBP that will allow successful treatment of patients that are currently unresponsive to drugs or suffer from intolerable side effects of drugs despite adequate control of blood pressure. Control of hypertension generally means the reduction of peak systolic pressure, diastolic pressure or mean arterial blood pressure substantially below the untreated levels. In HBP patients, experts believe that lowering the diastolic blood pressure by as little as 5 mmHg and/or the systolic blood pressure by as little as 10 mmHg will have a dramatic beneficial effect on the world population health. Since blood pressure is naturally variable over time, this invention may be applied to reduce HBP when it has reached clinically dangerous levels. The invention may be embodied as an implanted medical device that is self-sustaining over a period of many years and can be implanted by a minimally invasive surgery. For example, a fully implantable stimulation device having no elements of the implanted portion of the device across the skin may be employed. Skin is an important barrier to infection.

The invention addresses the remaining clinical need to control high blood pressure in patients that do not respond to drug medication. The invention may be applied to overcome the deficiencies of the devices previously proposed to treat hypertension. It is notable that while several devices for hypertension were proposed and there is a clear unmet clinical need, there are no such needed effective devices currently available on the market, and hypertension remains uncontrolled in many patients. The invention may be implemented with an electric stimulation device implantable in an uncritical location such as in an arm or a leg of the patient. The device stimulates a peripheral nerve or a muscle innervated by the peripheral nerve that sends sensory information back to the brain and is known to reduce blood pressure when stimulated. A particularly suitable nerve is the median nerve in the arm of a human. The physiologic link between stimulation of several points in the arm and the central control of the cardiovascular system is not well understood but the existence of such link has been confirmed in several scientific experiments with animals.

Cardiovascular regulation via a median nerve stimulation is described, for example, in Li et al., "Reversal of Reflex-Induced Myocardial Ischemia by Median Nerve Stimulation: A Feline Model of Electroacupuncture," Circulation 97(12), pp. 1186-94 (Mar. 31, 1998), hereby incorporated by reference.

In Abad-Alegria et al., "Objective assessment of the sympatholytic action of the Nei-Kuan acupoint," Am J Chin Med 2001; 29(2):201-10, authors described reduction of blood pressure after of Neiguan point acupuncture. In the terms of Western anatomy, the Neiguan point is located on the underside of the wrist two inches above wrist crease, between tendons of palmaris longus & flexor carpi radialis and is near the median nerve.

Similarly Chao et al., "Naloxone reverses inhibitory effect of electroacupuncture on sympathetic cardiovascular reflex responses," American Journal of Physiology. 276(6 Pt 2): H2127-34, 1999 June reported that in a cat with the drug induced reversible myocardial ischemia, electrical stimulation of the median nerves mimicking electroacupuncture of the Neiguan acupoint significantly improved ischemic dysfunction.

The device disclosed herein uses invasive nerve stimulation whereby electricity is passed through at least two implanted electrodes to stimulate nerves located near the targeted nerve. An example of such stimulation site can be located on the ventral side of the wrist (this anatomical position is sometimes referred to as the palmar side of the wrist). The treatment provided by the implanted device. One preferred site of stimulation is referred to in the acupuncture art as the Neiguan point, also sometimes referred to as: pericardium 6 point, Nei-Kuan, EH6, CP6, Neikuan, P6 or master point of the pericardium meridian or vascular meridian. The acupuncture point Neiguan (P6) is probably best known in the West as a treatment for nausea. It has been claimed in Western literature that not only standard acupuncture needling is effective for this application, but that one can use finger pressure massage (acupressure) at that site or even have the person wear a wristband that includes a bump that will press into Neiguan when positioned properly. In contrast, in China, Neiguan acupuncture is often used to treat cardiac disease such as chest pain.

The device for treatment of hypertension comprises an implanted stimulator and an implantable lead terminated with electrodes that apply electrical impulses. The basic implantable stimulator consists of a pacemaker-like titanium case enclosing the power source and a programmable circuitry that are used to create and regulate the electrical impulses. An extension lead attached to this generator carries the said electrical pulses to the electrodes that are implanted near the nerve to be stimulated. In the preferred embodiment of the invention the stimulation electrodes can be implanted in the muscle tissue, on the surface of the muscle under the skin, along the nerve trunk or in a blood vessel adjacent to the nerve. It may be necessary but not desired to place the electrode "cuff" on the nerve itself. Nerve cuffs increase the probability of an injury to the nerve that can lead to the loss of a sensory or motor function essential for the patient. Cuffs also have the known advantage of the best direction of the stimulation current. The physician places the connecting lead by tunneling a passage from the stimulation site to a location where the stimulator can be implanted in the tissue pocket usually on the torso of the patient.

Implantation of electrodes under the skin allows reducing the electric current requirements for stimulation and securing the position of the electrodes. The former is critical to conserve the battery energy. It is desired to have an implant that does not require replacement or recharging of the battery for ten years or more. Programmable electronics allows the physician to adjust the amplitude and patterns of stimulation to achieve the desired effect on blood pressure while keeping the stimulation current under the threshold of pain and muscle twitching. Programming is implemented by radio frequency communication so that the adjustments to the stimulation program can be made in the doctor's office.

It is known that the human body adapts to continuous nerve stimulation over extended periods of time. This phenomenon manifests in the gradual reduction or "resetting" of the initial response to stimulation. It is also known that, if a nerve is stimulated continuously, the power required for the desired duration of stimulation will exceed the amount that can be stored in an implanted battery. It is also known that in patients with hypertension the blood pressure swings up and down over the course of a day or in relation to stress and energy demands of the body. In the preferred embodiment, the nerve stimulation is not continuous. The stimulation is turned on and off periodically following either a preset time course or in response to a physiologic feedback such as the heart rate, blood pressure, and the arterial blood pulse pressure.

A peripheral nerve (preferably in the extremity of the patient) that requires simpler surgery than the carotid sinus nerve or the vagus nerve stimulation proposed by prior art. Also, unlike the carotid or vagus nerve stimulation, stimulation of a peripheral nerve cannot stop the heart or reduce blood pressure to the level where it can cause stroke, myocardial infarct or death.

SUMMARY OF THE DRAWINGS

A preferred embodiment and best mode of the invention is illustrated in the attached drawings that are described as follows.

DETAILED DESCRIPTION OF THE INVENTION

For the proposed clinical use, the capability of the invention is to control hypertension by invasively stimulating a peripheral nerve (such as the median nerve) with an implantable nerve stimulator.

Figure 1:
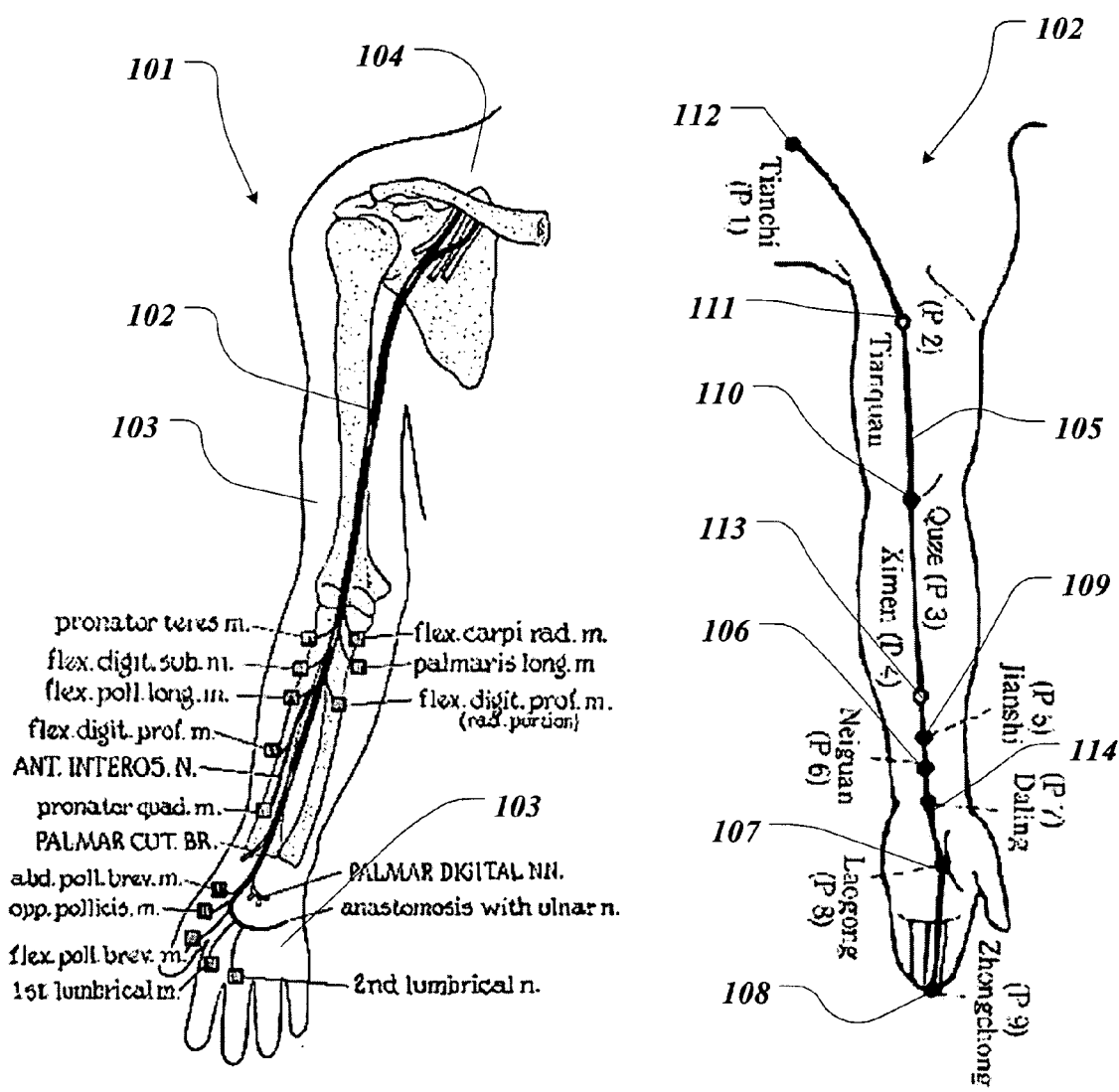
FIG. 1 illustrates the relationship between the anatomy of the median nerve in humans and the 9 acupuncture points of the pericardium meridian

FIG. 1 illustrates the relationship between the pericardium meridian 105, as defined by Chinese traditional acupuncture, and the median nerve 102. The left panel 101 shows the median nerve anatomy. The median nerve supplies most of the feeling in the hand, particularly to the thumb, index and middle fingers, the thumb half of the palm and the outer side of the hand. It also controls the movement of many of the muscles that bend the fingers, allowing the hand to grasp objects as well as pinch.

The right panel shows the Neiguan 106 point located on the forearm portion of the pericardium meridian 105 that has a total of nine standard acupuncture points. Although in the preferred embodiment of the invention the electrostimulation is applied to the Neiguan point, it is understood that the other eight points Tianchi 112, Tianguan 111, Quze 110, Ximen 113, Jianshi 109, Daling 114 Laogong 107 and Zhonghong 108 can be used instead or in combination with the Neiguan 106. Alternatively any other point along the median nerve 102 between the palm 103 and the collar bone 104 can be stimulated.

Figure 2:
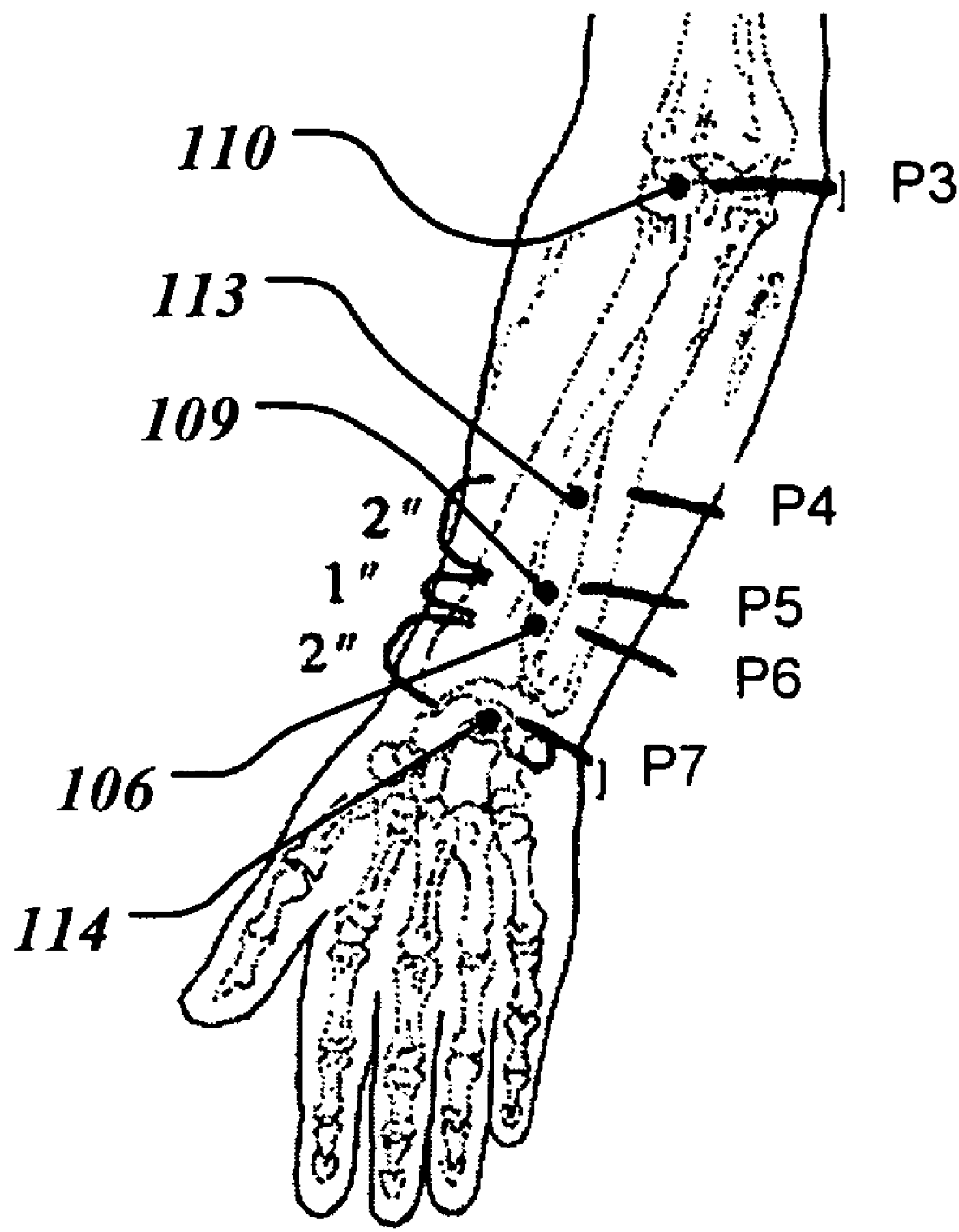
FIG. 2 illustrates the Neiguan point position

FIG. 2 further illustrates the Neiguan 106, Quze 110, Ximen 113, Jianshi 109, Daling 114 points in relation to the human arm anatomy. The segment of the median nerve defined by these points innervates multiple muscle groups in the arm as shown on the FIG. 1.

Figure 3:
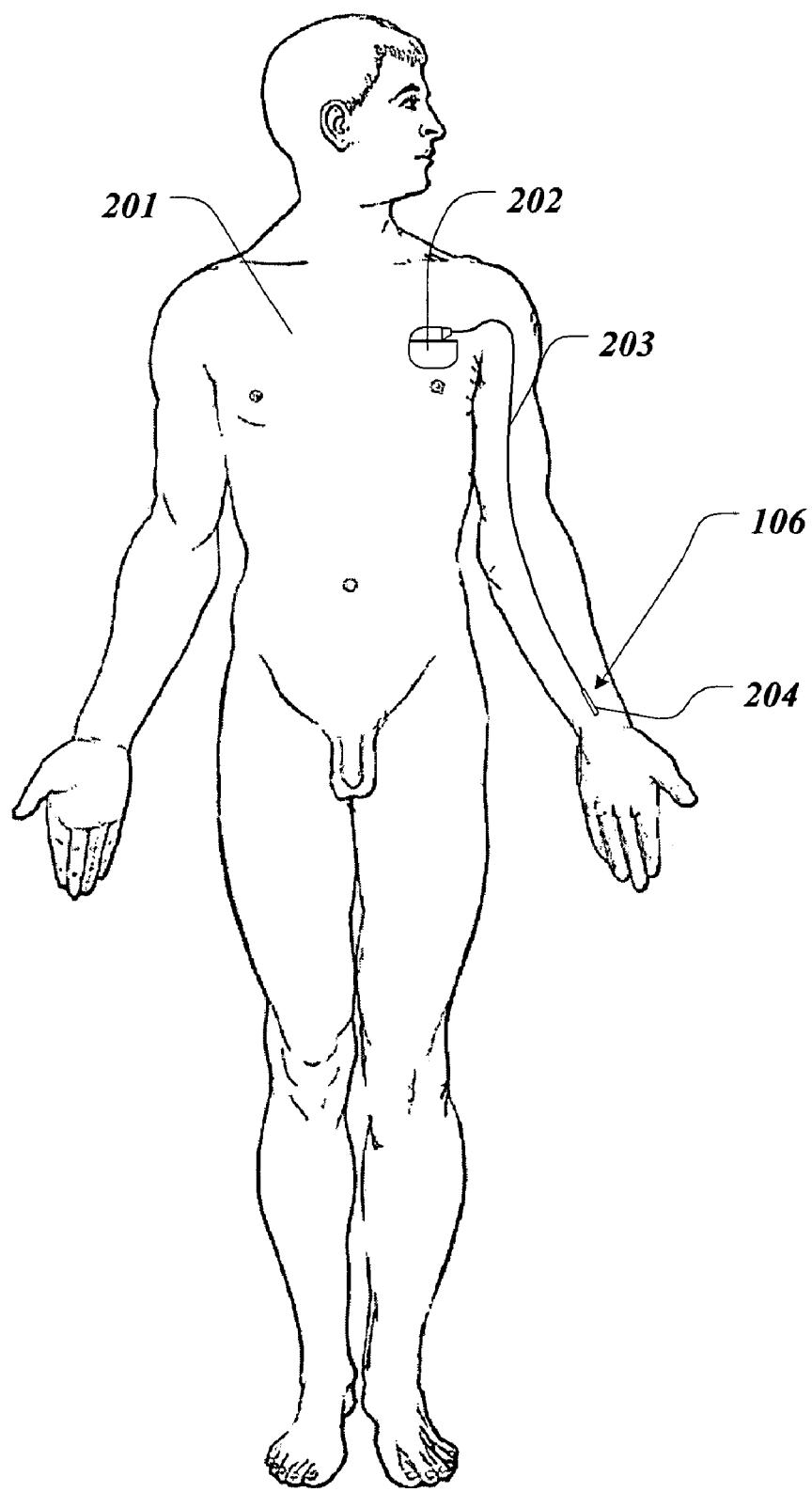
FIG. 3 illustrates the placement of the implantable electrostimulation device to treat hypertension

FIG. 3 shows a patient 201 treated with the invention. The stimulator 202 is implanted in a pocket in the patient's chest, similar to where a cardiac pacemaker is frequently implanted. The stimulator 202 is connected to the lead 203 equipped with the electrode tip 204. The electrode tip 204 is implanted in the proximity of the Neiguan 106. It is understood that the electrode 204 can be implanted anywhere along the median nerve between the points 112 and 108 (See FIGS. 1 and 2). The also can be more electrodes along the length of the lead that for example correspond to points P1 to P9 along the pericardium meridian 105. An example of an implantable nerve stimulator 202 is the Vagus Nerve Stimulation (VNS™) with the Cyberonics NeuroCybernetic Prosthesis (NCP®) System used for treatment of epilepsy. Other commercially available stimulators are the Genesis Implantable Pulse Generator manufactured by the Advanced Neuromodulation Systems, Inc. (Plano, Tex.) and used to control pain, and the Medtronic, Inc. (Minneapolis, Minn.) Synergy® Neurostimulation System. These three state-of-the-art stimulators are fully implantable, externally programmable and operate with a variety of implantable leads and electrodes adapted for long time implantation in the body. With some modifications, stimulators available from Medtronic, Cyberonics and Advanced Neuromodulation Systems can be adapted for this invention. Alternatively, a manufacturing company with right expertise can develop a dedicated stimulator for the invention if the parameters of stimulation are defined.

A lead is an insulated wire that is connected to a stimulator. The wire can include several insulated conductors from individual electrodes. Leads are extremely flexible in order to withstand the twisting and bending caused by body movement and/or movement by the heart itself in the case of cardiac pacemakers. Typically, there are four parts of a lead. The Connector Pin is the portion of the lead that is inserted into the connector block on the stimulator. The Lead Body is an insulated metal wire that carries electrical energy from the pacemaker to the heart. The Fixation Mechanism is the small mechanism near the tip of the lead that holds the lead electrodes to the muscle or other tissue. Electrode (at least one) is the bare or exposed electric contact located at the tip of the lead. The electrode delivers the electrical energy from the stimulator to the tissue. Medication can be added where a lead electrode touches the tissue. Regardless of whether a lead is placed on the nerve, muscle or connective tissue, the location where the lead touches the tissue naturally produces an inflammatory response. This response is similar to what is observed when the skin is scraped or cut: the area around the scrape is red and may result in a scar as your body repairs itself. By placing a steroid drug at the tip of the lead, some leads (such as for example the Medtronic CapSure pacing leads) reduce this inflammation. The steroid dose, typically 1 mg, is administered over a period of several weeks. The use of steroids can help extend stimulator battery life by almost 50%, because less scar tissue means lower resistance (lead impedance) and thus less current required for the electrical pulse that stimulates the nerve.

Figure 4:
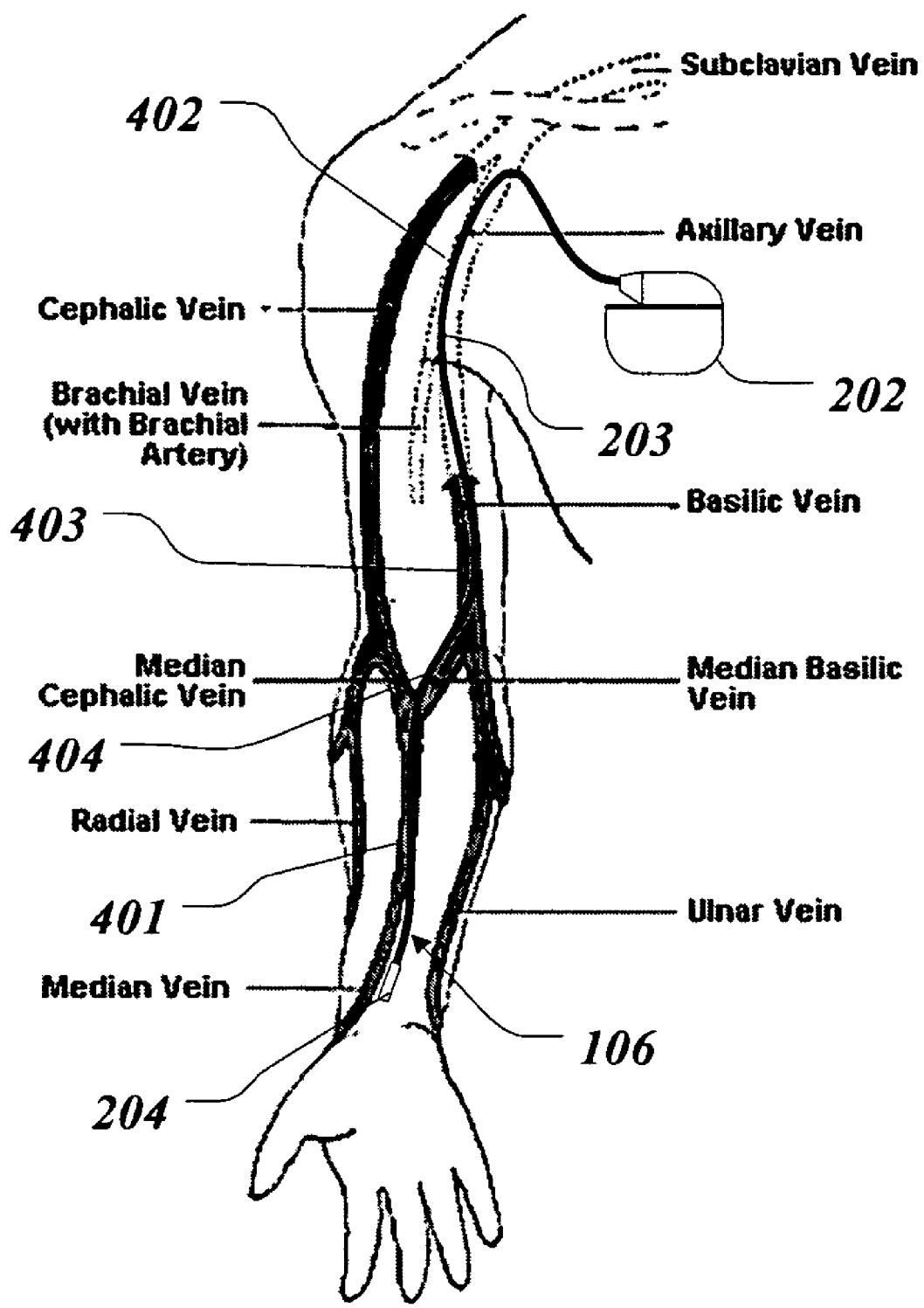
FIG. 4 illustrates the use of peripheral veins to place the lead

FIG. 4 shows an embodiment of the invention that takes advantage of the patient's venous system to connect the stimulator 202 to the stimulation point Neiguan 106. The lead 203 is inserted into a large vein in the proximity of the stimulator implantation site. The vein can be a subclavian or an axillary 402 vein. The lead 203 is threaded through the connecting veins such as the basilic vein 403, the median basilic vein 404 into the median vein 401 that is close to the Neiguan point 106. The electrode tip 204 can reside inside a small vein or in the tissue outside of the vein. The use of the venous route allows avoiding tunneling of tissue and surgical scars.

Suture, staples, hooks, barbs or screws, similar to ones used to secure pacemaker leads, can be used to anchor the lead and improve the electric contact with the stimulated tissue. The lead tip 204 can have one, two or more electrodes integrated in its design. The purpose of the electrodes is to generate the electric field sufficiently strong to influence traffic along the median nerve 102 (See FIG. 1). The lead thus placed is then connected to the implantable stimulator that is left in the body and the surgical sites are closed. Patients have the benefit of mobility and lower risk of infection with the implanted stimulator—lead system. Similar to the venous embodiment, an arterial system can be used. Surgical methods of implanting leads and stimulators using patient's veins, arteries and tissue tunneling are well known in the field of cardiac pacemaker placement and connecting.

Figure 5:
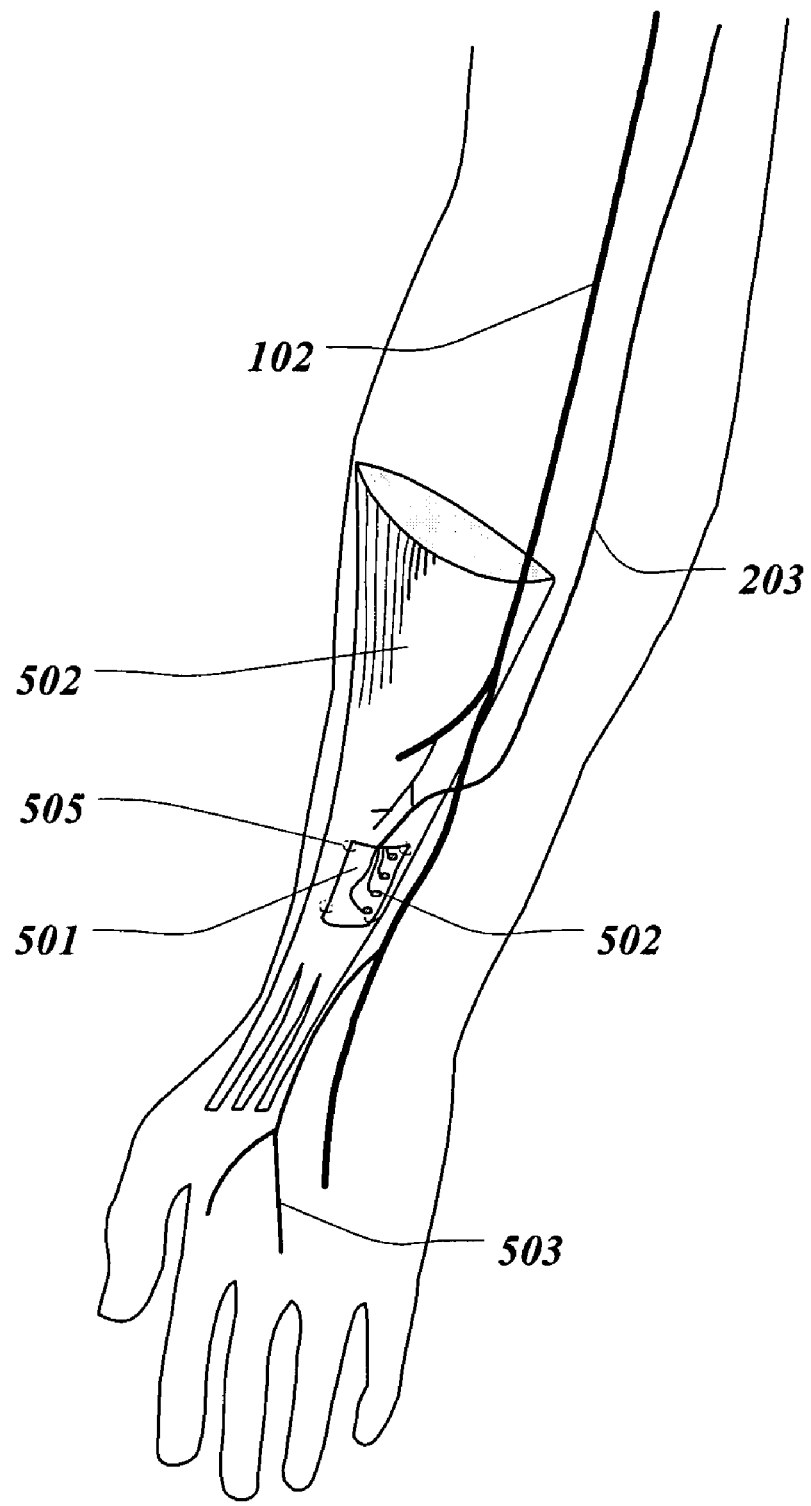
FIG. 5 illustrates the design of the muscle patch with electrodes

FIG. 5 illustrates an embodiment of the median nerve stimulation device for indirectly activating (stimulating) the median nerve 102 by stimulating the sensory nerves of a muscle. The stimulation electrodes (cathodes and anodes) 502 are integrated with a patch 501 that is attached to the surface of a muscle 504 in the patient's arm. The lead 203 connects the electrodes 502 to the stimulator. The patch 501 can be attached to the external surface of a muscle layer with suture 505 or staples or glue. Since the muscle 504 contracts, the patch 501 is made of a very flexible material and maintains contact with the muscle. It is notable that the median nerve 203 innervates the muscle 504. For example, in the forearm, the median nerve supplies: articular branches to the elbow joint muscular branches to pronator teres, and the superficial muscles which flex the wrist and fingers (i.e. palmaris longus, flexor digitorum superficialis), except for the medial half of flexor digitorum superficialis (which flexes the ring and little fingers) and flexor carpi ulnaris, which are both supplied by the ulnar nerve. In addition, the median nerve has two main branches in the forearm: the anterior interosseous nerve (which supplies most of the deep flexor muscles of the wrist, thumb and fingers), and the palmar cutaneous branch 503 of the median nerve (which forms the sensory supply to the skin of the palm of the hand). Any of the muscles listed above, when stimulated, will transmit sensory information to the brain by activating the median nerve.

Before the nerve stimulation can be implemented as a continuous chronic therapy several steps are essential. The electrode lead is placed at the stimulation site and connected to a stimulator. For testing purposes an external signal generator can be used instead of an implantable stimulator. Experimental stimulation patterns (characterized by electric current, pulse duration and frequency) are applied by the physician. At some level of stimulation (typically the electric current is gradually increased during the test) characteristic muscle twitching or pain is observed. This means that the level of stimulation should be lowed. It is practical to implement the level of stimulation that is just below the threshold of twitching or pain. After the test, the permanent stimulator can be implanted and the surgical sites closed. It can be expected that after some time the body's response to stimulation may change. The stimulator can be reprogrammed in the physician's office. The effectiveness of stimulation can be judged based on such physiologic parameters as: blood pressure, heart rate variability (measure of sympathetic nerve activity) or levels of hormones in blood.

Figure 6:
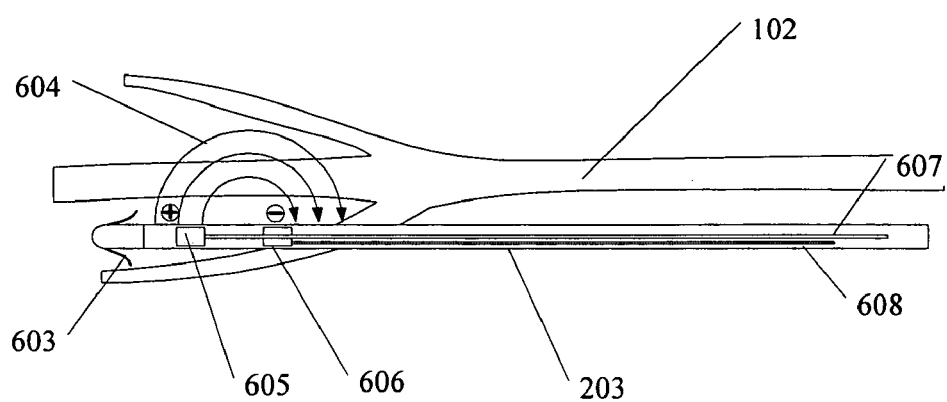
FIG. 6 illustrates the placement of the stimulation lead in relation to the nerve

FIG. 6 shows a simple tubular shape lead embodiment of the invention for bipolar stimulation of the median nerve 102. The stimulation lead 203 is a flexible device that is introduced into the close proximity of the nerve 102 and placed along the nerve trunk. The lead can be anchored to the surrounding tissue using a securing device 904. The securing device can be a barb or a screw if the permanent placement of the lead 903 is desired. The electric field 604 is induced by the electric current applied by the positively charged anode 605 and negatively charged cathode 606 electrodes. Electrodes are connected to the stimulator (not shown) by wires 607 and 608 that can be incorporated into the lead 203. An electric field 604 is induced in the tissue surrounding the nerve and creates the desired local depolarization of the segment of the nerve trunk 102 situated in the close proximity of the cathode. More electrodes can be places along the length of the lead to achieve different selective patterns of stimulation. The lead is shown as bipolar. It is possible to have only one electrode (for example, a cathode) per lead. The second electrode (anode) can be implanted separately with a different lead in a different location. Alternatively the metal case of the stimulator itself can be used as an electrode.

The wire lead 203 can be inserted into the fascia surrounding the nerve, threaded through the muscle layers or anchored inside a small blood vessel (vein or artery) that supplies blood to the muscle that is innervated by the median nerve. Closer to the palm of the hand, the median nerve is located between the tendons of the palmaris longus and the flexor carpi radialis. The lead 203 can be inserted between the tendons and affixed to tissue.

The lead 203 can be inserted surgically, percutaneously or transvenously. In common pain control therapy applications, similar percutaneous leads are small diameter tubes that are typically inserted into the human body through a Tuohy (non-coring) needle, which includes a central lumen through which the lead is guided. Typically, the electrodes 605 and 606, also called contacts, on percutaneous leads are cylindrical metal structures, with a diameter of approximately 1 mm and a length of 4 to 10 mm. Half of each of these electrodes, facing away from the tissue of interest, is not useful in delivering therapeutic current and merely increases the leakage current that would drain the stimulator battery. Thus, the surface area of electrodes facing the excitable tissue (such as the nerve or the innervated muscle) is small, typically 3.0 to 10.0 square mm. The minimal required electrode surface area is determined by the stimulation current required to excite cells delivered with each electrical pulse and the charge density at which damage may occur to the tissue or the electrode itself.

The lead 203 can be also similar to a paddle lead design known in the field of nerve stimulation. Paddle leads, like Model 3596 Resume Lead, Model 3982 SymMix Lead or Model 3991 Transverse Tripole Lead of Medtronic, Inc., have been developed to offer improved therapy over some aspects of percutaneous leads. Paddle leads include a generally two-dimensional array of electrodes on one side of a flat insulating body shaped as a flat strip, for providing electrical stimulation to excitable tissue and minimizing the leakage current. A paddle design allows electrodes to be considerably wider than percutaneous leads, up to 4.0 mm or more. Two-dimensional arrays of electrodes allow programming of active sites and better control of the electric field distribution. Larger surface area of electrodes allows safe delivery of higher stimulation currents. Paddle leads are generally placed surgically.

Figure 7:
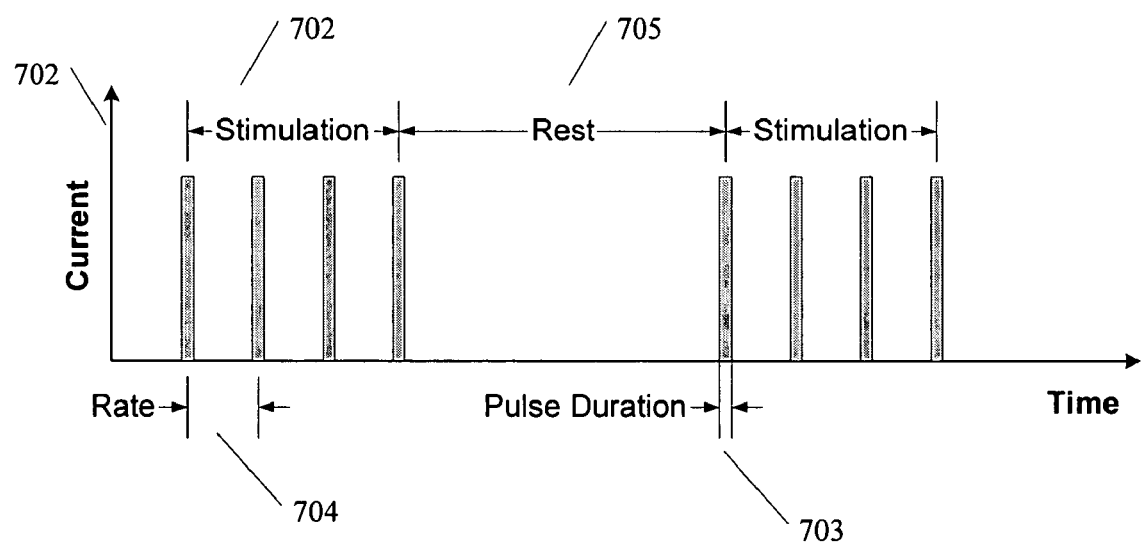
FIG. 7 illustrates the pattern of nerve stimulation with electric current pulses

FIG. 7 illustrate a stimulation pattern used in the preferred embodiment of the nerve stimulation device. The stimulation pattern achieves two objectives: a) effective stimulation of the nerve and b) power conservation. The electric current 701 needed for nerve stimulation is typically on the order of 0.1 to 5 milliamps (mA). Experience with the Cyberonics NeuroCybernetic Prosthesis shows that stimulation currents of 0.5 to 3 mA are well tolerated by patients (i.e., the magnitude of stimulation required to achieve a physiologic or clinical outcome does not cause pain or other adverse events). The stimulation lead impedance (resistance to current flow between electrodes) in clinical applications can be expected to be between 500 to 1,000 ohms. Under some circumstance, it can be as high as 3,000 ohms. Impedance of stimulated tissue between the lead electrodes (See 605 and 606 on FIG. 6) can change over time mostly due a change in capacitance. It is preferred to have a constant current stimulator that maintains a specified current between its output electrodes, regardless of the impedance of the load that is connected between the electrodes. Design of such constant current electronic circuits is well known in the field of nerve stimulation.

It is known from animal and human research that a sequential train of short duration electric pulses 702 is the best way to achieve the stimulation of a peripheral nerve. Duration 703 of stimulation pulses can range from tens of microseconds to tens of milliseconds, with the most commonly used pulse duration being 0.5-1.0 milliseconds. Since the magnitude and duration of the pulse duration have a profound effect on battery life, it is desired to adjust pulses to the shorted effective duration. At the same time, over a range extending roughly from 0.05 to 1 ms, changes in duration have a similar effect to changes in the current. For example, if the maximum current from a stimulator is too small to evoke a particular response with a 0.2 ms pulse, an increase to 0.5 or 1 ms may well be effective. In nerve stimulation, there is rarely much advantage in using pulses longer than 2 ms. For direct stimulation of certain smooth muscles though, a pulse width as long as 10 ms has been recommended. Effective peripheral nerve stimulation has been achieved at the frequency as low as 1 Hz (rate 704 is equal to one second between pulses). For all practical purposes, the terms rate and frequency are equivalent and indicate the spacing between periodic stimulation pulses. Frequencies in the range of 1 to 50 Hz have been successfully used both in electroacupuncture and in nerve stimulation. To conserve the battery life it is desired to use the lowest effective stimulation frequency.

For example, the stimulator can be equipped with a relatively large implantable lithium ion pacemaker battery (available from Wilson Greatbatch Technologies, Inc. Clarence, N.Y.) that weights 35 grams. Such battery can store 10.5 watt-hours (wh) of energy. This means that the stimulator can consume approximately 10.5 watts of power over 1 hour or 0.105 watts over 100 hours and so on before it runs out of energy. It is desired to have an implantable stimulator that will operate without battery change for 5 to 10 years or even longer. A smaller battery is always desired for patient's comfort; therefore the task of conserving stimulation energy is most important.

Fortunately, continuous stimulation is not necessary and not desired for treatment of hypertension. Experience with acupuncture shows that the daily and even weekly sessions of nerve stimulation as short as 20-30 minutes can have a significant therapeutic effect. If 4 sessions of 20 minutes per day are performed automatically with the electric stimulation parameters listed above, the pacemaker battery will last 10 years or more. FIG. 7 shows stimulation periods 702 followed by rest periods 705. Stimulation period and stimulation duration are the equivalent terms and describe the period of time during which the stimulation is on. The stimulation periods are followed by rest periods during which the stimulation is off.

In view of the considerations listed above, a programmable stimulator for stimulating the median nerve to treat hypertension can have, for example, the following set of programmable parameters or settings:

| Output current | 0 to 15 mA |
|---|---|
| Stimulating frequency | 1 to 200 Hz |
| Pulse width | 0.05 to 2 ms |

Although the proposed stimulator is capable of pulse frequency of 1 to 200 Hz it is expected that the frequency in the range of 1 to 5 Hz is most effective for the treatment of hypertension. It is also expected that the stimulation current will be most effective in the range of 1.5 to 3.5 mA and the pulse width in the rage of 0.1 to 0.5 ms. This selection of preferred parameters is based on the experience with the stimulation of afferent nerves in animals.

Figure 8:
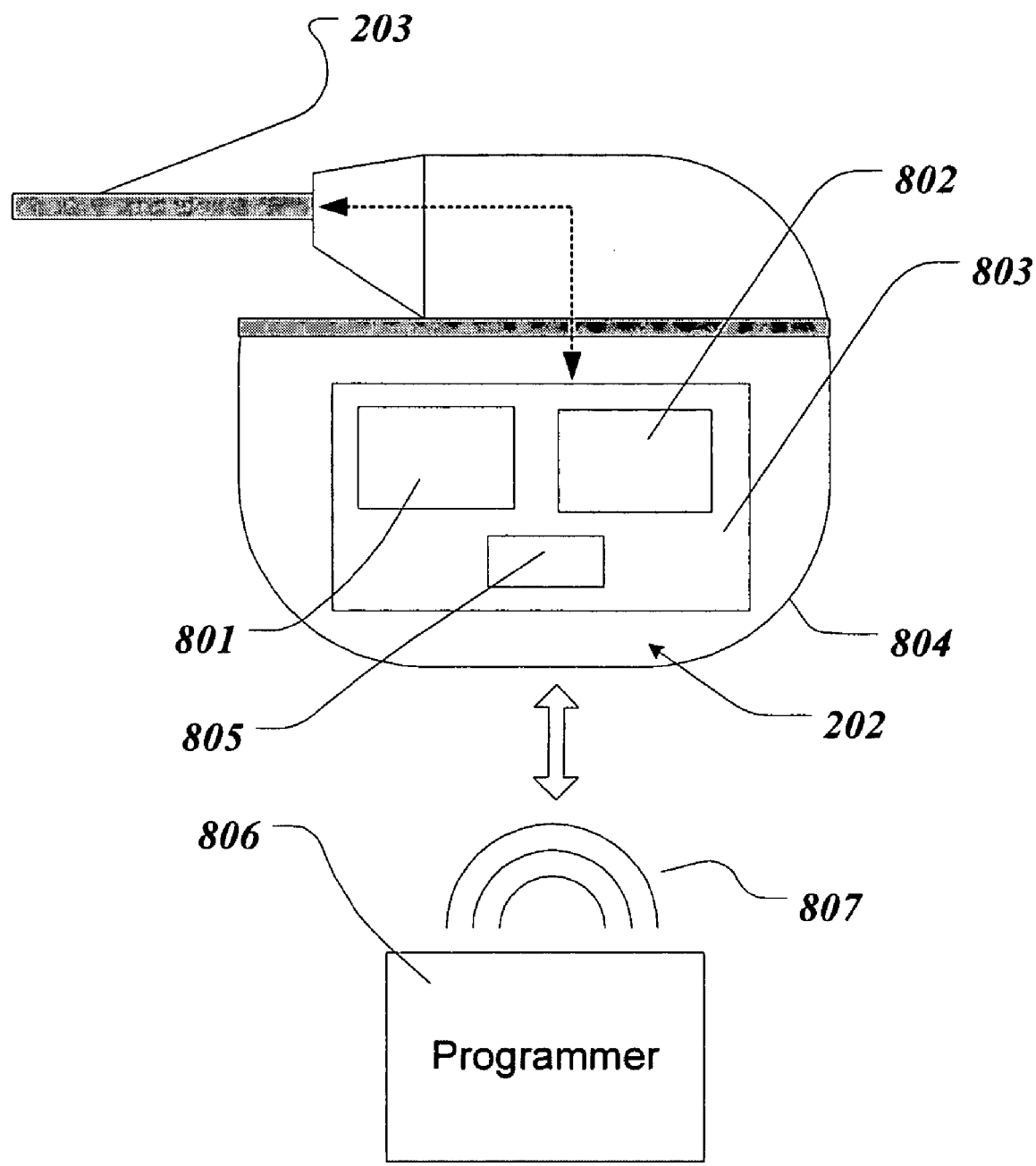
FIG. 8 illustrates the design of the implanted stimulator

FIG. 8 schematically illustrates the basic design of the nerve stimulator 202. The stimulator is enclosed in the titanium case 804. Inside the stimulator case is the electronic circuitry 803. The circuitry includes as a minimum: a battery 801, a microprocessor 802 and a programming interface 805. The electronics are connected to the lead 203. The lead can be used to stimulate tissue and to conduct electric signals from sensors. The stimulator can have more than one lead.

Programming of the stimulator can be achieved using traditional radio frequency communication 806. Alternatively, different stimulation parameter sets (also called patterns) stored in the ROM data area of the processor can be selected after the device had been implanted by directing a sequence of high intensity light flashes through the skin. The flashes are detected by a phototransistor in the implant and counted by the processor; the selected stimulation pattern is then initiated. The programmer 806 is an external device kept in the physician's office. The physician can use it to interrogate the microprocessor, collect information and change the parameters of stimulation.

The all-important power savings in a stimulator begins with a very low power microprocessor 802. The processor is a key internal part of the implanted stimulator 202. The processor need not be high performance device; processors like the RCA 1802 and the Motorola 6805 can be used in versions updated to run on lower voltages. To keep the processors' power consumption to a bare minimum, pacemaker designers strip away every feature and function that isn't absolutely essential. And because the workload on a pacemaker processor isn't heavy, the clock speed is low (typically 3-5 MHz) to further reduce power consumption. Code storage typically requires about 40 kbytes of ROM. Lately the continuing progress in commercial integrated microcontrollers introduced new devices such as a commercial microcontroller PIC16LC84 (Microchip Technology Inc. Chandler, Ariz.) with extremely low power consumption. It is possible that the stimulator based on such device will draw on average less than 50 microamps of operating current from a single integral 3V lithium cell. Stimulation patterns can be stored in the integral EEPROM data area of the PIC, including the sleep mode patterns.

For power savings, the processor remains in sleep mode between stimulation periods and in reduced power mode between stimulation pulses. Processing begins when a sensor in the pacemaker detects an event (such as an increased blood pressure, heart rate) or a pre-programmed clock time interval elapses. Still more power savings accrue through the use of smart stimulation algorithms that provide stimulation only when necessary, such as when blood pressure or pulse pressure is high. If a sensor determines that the blood pressure is acceptable, which is the case most of the time for many hypertensive patients, then the stimulator doesn't intervene, thus conserving battery power.

Stimulator can also apply stimulation to the nerve during the patient's sleep or rest. It can become active only during a predetermined, fixed time period—from 10 p.m. to 6 a.m., for example. Alternatively the stimulator can have sensors that detect physical activity and the frequency and depth of breathing. For example, a motion sensor bonded to the inside of the stimulator metal case (such as an accelerometer) detects pressure waves caused by muscle movement or body motion. Other sensors that can be used in the stimulator to start and stop stimulation include devices that measure body temperature, changes in body acidity, and pressures inside and outside of blood vessels.

Figure 9:
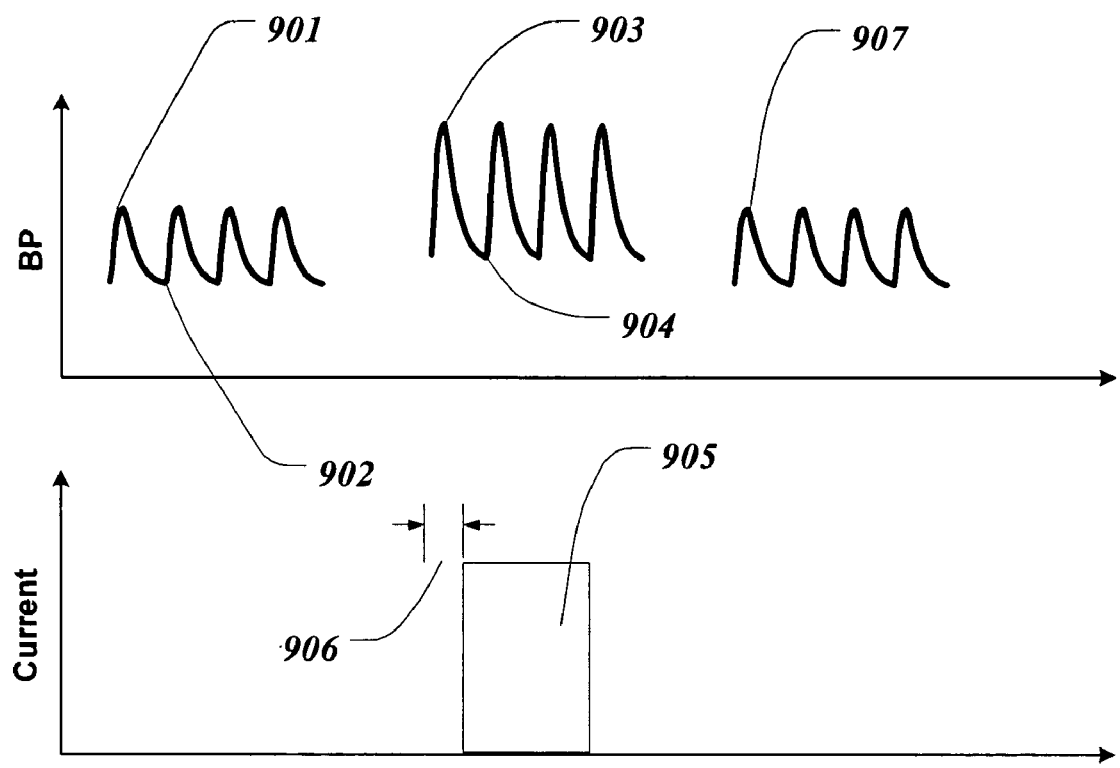
FIG. 9 illustrates the blood pressure feedback control of stimulation

FIG. 9 illustrates automatic stimulation of the peripheral nerve in response to blood pressure (BP) elevation. Blood pressure is monitored continuously by an implanted blood pressure sensor for systolic 901 and diastolic 902 values. The stimulation 905 can be automatically turned on in response to the systolic 903, diastolic 904 or mean BP exceeding the program threshold. Alternatively a sudden and sustained rise of BP over the historic values, stored in the processor memory, can be a trigger signal for stimulation. A programmed delay in detecting the BP rise 906 is used to ensure that the BP rise is not a short or transient phenomenon. Alternatively, a rise of pulse pressure can be used as a trigger signal to start a stimulation period. Pulse pressure is defined as a difference between the systolic 901 and diastolic values 902. There is an advantage to this method, since pressure sensors tend to drift over time and lose the correct zero pressure calibration. In addition, BP measurement is subject to changes of the atmospheric pressure that are not easy to detect with an implanted device. The pulse pressure is insensitive to drift and atmospheric pressure fluctuations, and therefore is the more robust index of the onset of the hypertension. There is some scientific evidence that the increase of pulse pressure indicates the increase of clinically significant systolic pressure in hypertensive patients. Stimulation 905 can be activated as described for a prescribed period of time or continue until the blood pressure 907 is reduced. The patient's heart rate, or an increase or decrease of the heart rate, is yet another alternative feedback for the automatic activation or inhibition of nerve stimulation, respectively. Monitoring the electrocardiogram of a patient or counting the blood pressure pulsations are two accepted ways of measuring the heart rate. The electrocardiogram can be monitored using additional electrodes mounted on the stimulator lead. Suitable implantable pressure sensors are described in the U.S. Pat. No. 5,564,434 "Implantable capacitive absolute pressure and temperature sensor"; in the U.S. Pat. No. 6,171,252 "Pressure sensor with increased sensitivity for use with an implantable medical device" and the U.S. Pat. No. 6,221,024 "Implantable pressure sensor and method of fabrication." These sensors are suitable for integration in a lead for use with a body implantable medical device. The sensing element of the pressure monitoring lead will be implanted in an artery of the patient preferably in the central body.

Figure 10:
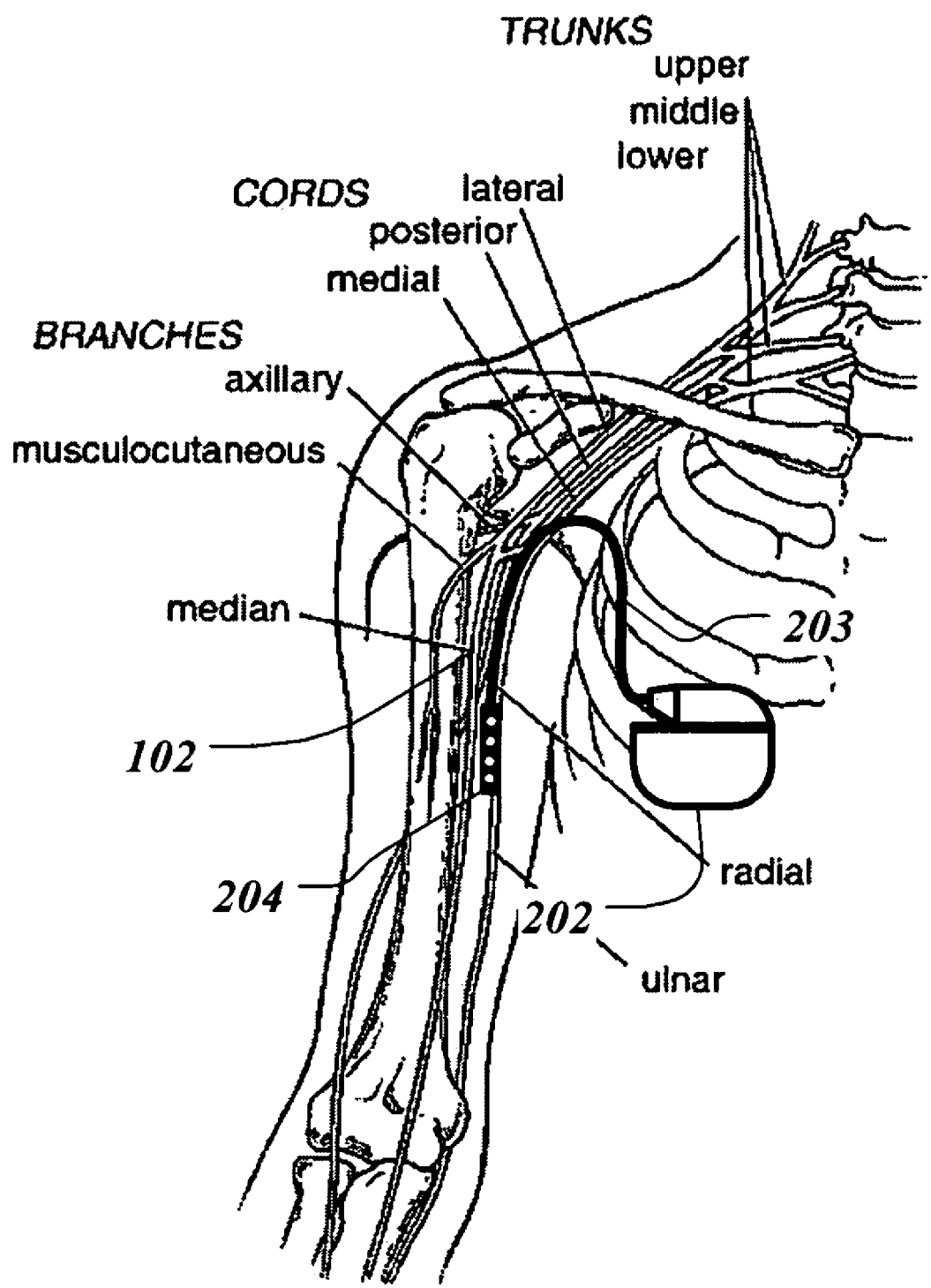
FIG. 10 illustrates an alternative placement of the stimulation lead electrodes for the median nerve embodiment

FIG. 10 illustrates an alternative placement of the median nerve stimulation electrodes. Electrodes 204 on the lead 203 are in placed in proximity of the median nerve 102 close to the patient's shoulder where the median nerve originates from the brachial plexus. The brachial plexus is found partly in the neck, but mainly in the axilla (armpit). This configuration has an advantage of the shorter lead and tunneling distance (compared to the stimulation of the Neiguan point).

Figure 11:
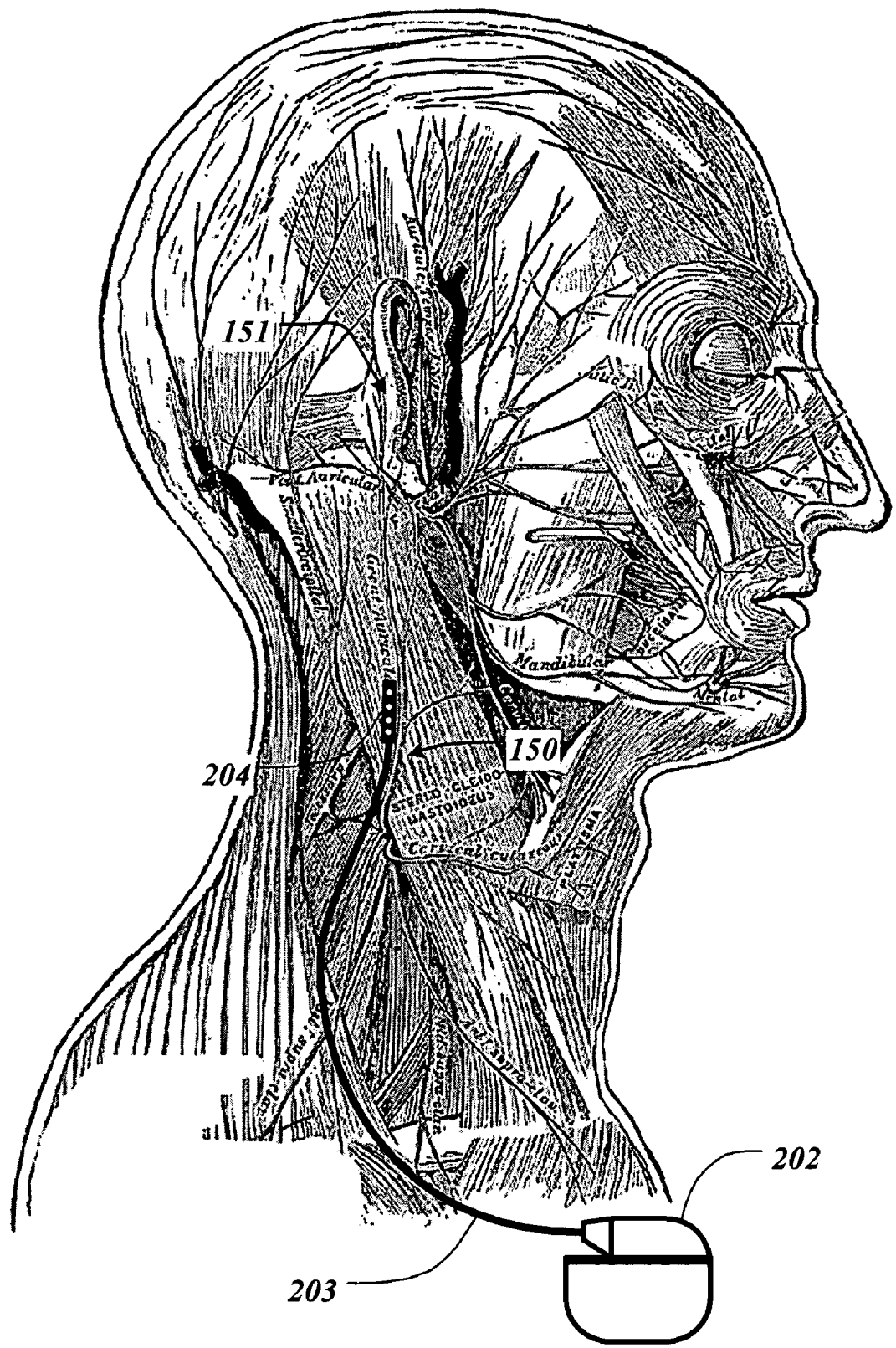
FIG. 11 illustrates the stimulation of an auricular nerve

FIG. 11 shows an alternative peripheral nerve stimulation embodiment to treat hypertension by stimulation of the auricular nerve. It is known from the traditional Chinese acupuncture that needling of several acupoints in a person's ear leads to the reduction of blood pressure. For example, Huang HQ et al. in the "Improvement of blood pressure and left cardiac function in patients with hypertension by auricular acupuncture", Chinese Journal of Modern Developments in Traditional Medicine, Nov., 11, 1991(11):654-6, 643-4, described 30 patients with hypertension, whose blood pressure was lowered by the "heart point of ear" needling. Williams T et al. in "Effect of AP-point stimulation on diastolic blood pressure in hypertensive subjects: a preliminary study", Physical Therapy July 71(7):523-529, studied electroacupuncture of 4 specific antihypertensive points (LV03, ST36, LI11, and the Groove behind the ear for Lowering Blood Pressure) in order to determine the effect of this stimulation on diastolic blood pressure in 10 subjects with diastolic hypertension. Repeated-measures analysis of variance showed an immediate and significant reduction of diastolic blood pressure post stimulation.

FIG. 11 shows the lead electrode 204 placed near the auricular nerve 150 in the neck of the patient. The auricular nerve innervates multiple sensory nerve endings in the ear. The stimulator 202 is implanted in the patient's torso (not shown) and connected to the electrodes 204 by the lead 203.

Figure 12:
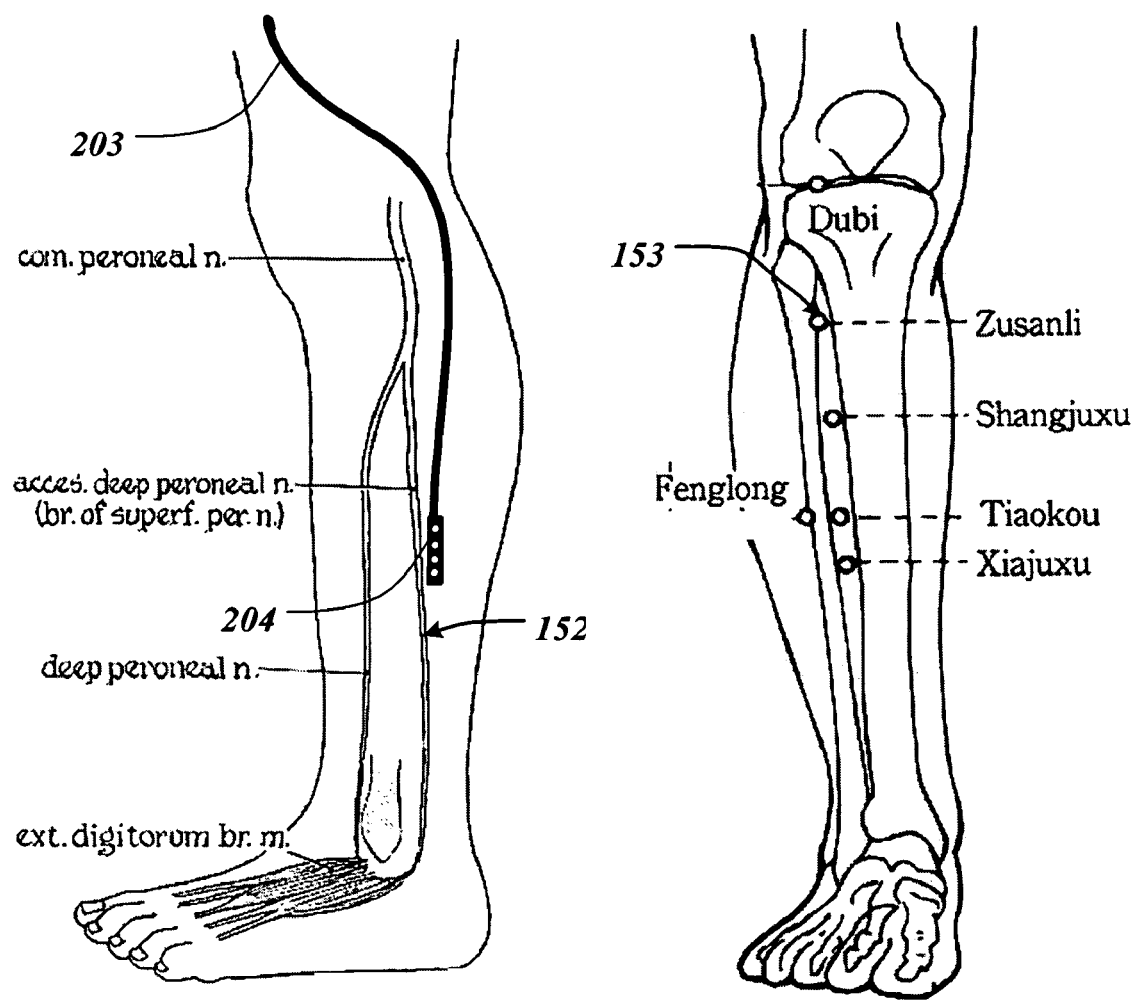
FIG. 12 illustrates the stimulation of a peroneal nerve

FIG. 12 shows the peroneal nerve embodiment of the invention. The peroneal nerve originates in the lumbosacral plexus from the roots of L4, 5, and S1, 2. After it leaves the pelvis the nerve travels down the front and side of the leg on its way to the foot. It runs along the lateral (outer) side of the knee and passes over the head of the fibula. The stimulation electrodes 204 are implanted in the leg of the patient near the deep peroneal nerve 152. FIG. 12 also shows the location of the traditional acupuncture point Zusanli associated with blood pressure control along with the Neiguan. It has been speculated that the Zusanli acupuncture results in the stimulation of the deep peroneal nerve (DPN) that has a known blood pressure reducing function. Effects of leg muscle and nerve stimulation and leg point acupuncture on the blood pressure were in scientific literature. Li Li, Yin Xiang et al. in "Influence of electroacupuncture on stress-induced hypertension and its mechanism", International Congress Series 1238 (2002) 97-100, and Peng Li in "Neural mechanisms of the effect of acupuncture on cardiovascular disease," International Congress Series 1238 (2002) 71-77, studied the influence of Zusanli acupuncture on blood pressure in rats and linked it to the stimulation of the deep peroneal nerve. Simulators or pulse generators used in the preferred embodiment utilize traditional flexible leads with electrodes. It is understood that advanced electronic technology and miniaturization allows construction of much smaller "microstimulators", such as a Bion manufactured by Advanced Bionics of Sylmar, Calif. The Bion's small size allows the entire device to be deployed directly next to the target of stimulation (such as for example a median nerve). Traditional neurostimulation devices consist of an implantable pulse generator (IPG) and electrode lead. Due to the large size of conventional IPGs, this component must be placed away from the site of stimulation in areas such as the chest, abdomen, or buttocks. The electrode lead and often a lengthy extension must then be tunneled under the skin to reach the stimulation site. Implantation of traditional devices involves extensive surgery, sizable scarring, and the possibility of a prominent bulge under the patient's skin. The Bion implantation is a sutureless procedure that uses a set of custom needlelike insertion tools 4 mm in diameter, leaving no visible scar or bulge.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for treating hypertension in a human patient comprising:
   implanting a nerve stimulation device proximate to at least one peripheral nerve in an extremity of the patient, wherein the implanting is at least partially performed by inserting a lead into the fascia surrounding the nerve; and
   applying a stimulation signal generated by the device to the peripheral nerve to control hypertension so as to avoid pain or twitching of a muscle in the extremity caused by the stimulation, the signal being applied repeatedly over a period of time to reduce blood pressure.

2. The method as in claim 1, wherein the peripheral nerve is one of a group consisting of a median nerve, a peroneal nerve, and deep peroneal nerve.

3. The method as in claim 1, wherein the stimulation signal further comprises electric pulses having a frequency in a range of 1 to 5 Hz.

4. The method as in claim 1, wherein the stimulation signal is applied based on a physiologic feedback.

5. The method as in claim 1, wherein the stimulation device is implanted on a surface of a muscle innervated by the peripheral nerve.

6. The method as in claim 1, wherein the stimulation device is implanted along the peripheral nerve.

7. The method as in claim 1, wherein the stimulation device is implanted proximally to a Neiguan point or points Tianchi, Tianguan, Quze, Ximen, Jianshi, Daling, Laogong, and Zhonghong in an arm of the patient.

8. The method as in claim 1, wherein the stimulation device is implanted proximally to a Zusanli point in a leg of the patient.

9. The method as in claim 1, wherein the stimulation signal is applied with electric pulses at a current of 0.5 to 5 mA and a duration of 0.25 to 0.5 ms; and wherein the stimulation signal is applied for 20 to 60 minutes followed by a rest period.

10. A method for treating hypertension in a human patient comprising:
    implanting a nerve stimulation device proximate to a median nerve in a wrist of the patient, wherein the implanting is at least partially performed by inserting a lead between tendons of the wrist in proximity to the nerve; and
    applying a stimulation signal generated by the device to the peripheral nerve to control hypertension so as to avoid pain or twitching of a muscle in the extremity caused by the stimulation, the signal being applied repeatedly over a period of time to reduce blood pressure.

11. The method as in claim 10, wherein the stimulation signal further comprises electric pulses having a frequency in a range of 1 to 5 Hz.

12. The method as in claim 10, wherein the stimulation signal is applied based on a physiologic feedback.

13. The method as in claim 10, wherein the stimulation device is implanted on a surface of a muscle innervated by the median nerve.

14. The method as in claim 10, wherein the stimulation device is implanted along the median nerve.

15. The method as in claim 10, wherein the stimulation signal is applied with electric pulses at a current of 0.5 to 5 mA and a duration of 0.25 to 0.5 ms; and wherein the stimulation signal is applied for 20 to 60 minutes followed by a rest period.

* * * * *

UNITED STATES PATENT AND TRADEMARK OFFICE
CERTIFICATE OF CORRECTION

PATENT NO. : 7,373,204 B2  
APPLICATION NO. : 10/921162  
DATED : May 13, 2008  
INVENTOR(S) : Mark Gelfand et al.

Page 1 of 1

It is certified that error appears in the above-identified patent and that said Letters Patent is hereby corrected as shown below:

On the title page, item [56]:
Column 2 (Other Publications), Line 2, delete "Internation" and insert
-- International --, therefore.

Signed and Sealed this

Sixteenth Day of September, 2008

JON W. DUDAS  
*Director of the United States Patent and Trademark Office*

UNITED STATES PATENT AND TRADEMARK OFFICE
CERTIFICATE OF CORRECTION

PATENT NO. : 7,373,204 B2 Page 1 of 1
APPLICATION NO. : 10/921162
DATED : May 13, 2008
INVENTOR(S) : Gelfand et al.

It is certified that error appears in the above-identified patent and that said Letters Patent is hereby corrected as shown below:

On the Title Page Item (56) (Other Publications), Line 2, delete "Internation" and insert -- International --.

Signed and Sealed this

Thirtieth Day of September, 2008

JON W. DUDAS
*Director of the United States Patent and Trademark Office*